United States Patent
Tachiya et al.

(10) Patent No.: US 9,061,949 B2
(45) Date of Patent: Jun. 23, 2015

(54) METAL COMPONENT ABSORPTION ENHANCER IN PLANT

(75) Inventors: Naohisa Tachiya, Satte (JP); Shigeyuki Funada, Satte (JP); Masahiro Ishizuka, Tokyo (JP)

(73) Assignee: COSMO OIL CO., LTD., Tokyo (JP)

( * ) Notice: Subject to any disclaimer, the term of this patent is extended or adjusted under 35 U.S.C. 154(b) by 876 days.

(21) Appl. No.: 12/669,637

(22) PCT Filed: Sep. 5, 2007

(86) PCT No.: PCT/JP2007/067329
§ 371 (c)(1),
(2), (4) Date: Jan. 19, 2010

(87) PCT Pub. No.: WO2009/013841
PCT Pub. Date: Jan. 29, 2009

(65) Prior Publication Data
US 2010/0203159 A1    Aug. 12, 2010

(30) Foreign Application Priority Data

Jul. 20, 2007   (JP) ................................. 2007-189879

(51) Int. Cl.
| | | |
|---|---|---|
| *A01N 37/44* | (2006.01) | |
| *A01N 59/16* | (2006.01) | |
| *A01N 59/20* | (2006.01) | |
| *C05D 9/00* | (2006.01) | |
| *C05F 11/10* | (2006.01) | |
| *A01N 59/00* | (2006.01) | |
| *C05D 3/00* | (2006.01) | |
| *C05D 5/00* | (2006.01) | |

(52) U.S. Cl.
CPC ............... *C05F 11/10* (2013.01); *A01N 59/00* (2013.01); *A01N 59/20* (2013.01); *C05D 9/00* (2013.01); *A01N 59/16* (2013.01); *C05D 5/00* (2013.01); *A01N 37/44* (2013.01); *C05D 3/00* (2013.01)

(58) Field of Classification Search
None
See application file for complete search history.

(56) References Cited

U.S. PATENT DOCUMENTS

| | | | | |
|---|---|---|---|---|
| 5,298,482 | A * | 3/1994 | Tanaka et al. ................. | 504/320 |
| 5,504,055 | A | 4/1996 | Hsu | |

FOREIGN PATENT DOCUMENTS

| | | |
|---|---|---|
| CA | 2278383 A1 | 1/2001 |
| CN | 1132592 A | 10/1996 |
| EP | 0514776 A1 | 5/1992 |
| EP | 0698345 A1 | 2/1996 |
| EP | 0714600 A2 | 6/1996 |
| EP | 1413303 A1 | 4/2004 |
| EP | 2130435 A1 | 12/2009 |
| JP | 4-338305 A | 11/1992 |
| JP | 6-271405 A | 9/1994 |
| JP | 8-225408 A | 9/1996 |
| JP | 2007-238482 A | 9/2007 |

OTHER PUBLICATIONS

Watanabe et al., Enhancement of growth and fruit maturity in 2-year-old grapevines cv. Delaware by 5-aminolevulinic acid, Plant Growth Regul. (2006), vol. 49, pp. 35-42.*
Watanabe, et al., "Growth and Fruit Quality Enhancing of 2 Years Old Grapevine "Delaware" by 5-Aminolevulinic Acid", The 37th General Meeting of the Japanese Society for Chemical Regulation of Plants, 2002, pp. 85 to 86 Abstract.
Quarterly magazine "Hiryo", 2005, No. 102, pp. 122 to 127.
Japanese Office Action dated Dec. 21, 2010 issued in a counterpart application No. 2007-227358.
Extended European Search Report issued on Mar. 22, 2011 in the corresponding European Patent Application No. 07806771.7.
Office Action dated Oct. 5, 2011 from the European Patent Office in counterpart European application No. 07806771.7.
Yoshida, R., et al., "Effect of 5-Aminolevulinic Acid on Growth and Nutrient Uptake of Leaf Vegetables in Alkaline Soil", Proceedings of Annual Meeting of Society for Chemical Regulation of Plants, 2002, pp. 87-88.
International Search Report for PCT/JP2007/067329 dated Oct. 2, 2007 [PCT/ISA/210].
Office Action dated Mar. 29, 2012 issued by the State Intellectual Property Office of P.R. China in counterpart Chinese Application No. 200780053828.1.
Chinese Office Action dated Oct. 17, 2012 issued by the State Intellectual Property Office of P.R. China in corresponding Chinese Application No. 200780053828.1.

* cited by examiner

*Primary Examiner* — Abigail Fisher
*Assistant Examiner* — Frank Choi
(74) *Attorney, Agent, or Firm* — Sughrue Mion, PLLC

(57) ABSTRACT

A metal component absorption enhancer which enhances the absorption of at least one metal component selected from the elements belonging to groups 2 to 12 in the third to fourth periods when a plant grows. The metal component absorption enhancer contains 5-aminolevulinic acid or a derivative thereof represented by the following general formula (1), or a salt thereof as an active ingredient:

$$R^2R^1NCH_2COCH_2CH_2COR^3 \quad (1)$$

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group, an acyloxy group, an alkoxycarbonyloxy group, an aryloxy group, an aralkyloxy group, or an amino group, and is used for performing a treatment with 0.001 to 20 ppm of the 5-aminolevulinic acid, the derivative thereof, or the salt thereof per each time.

2 Claims, 4 Drawing Sheets

METAL COMPONENT ABSORPTION ENHANCER IN PLANT

TECHNICAL FIELD

The present invention relates to a metal component absorption enhancer which enhances the absorption of at least one metal component selected from the elements belonging to the groups 2 to 12 in the third to fourth periods when a plant grows.

BACKGROUND ART

Among essential elements for growth of a plant, carbon, hydrogen, and oxygen are supplied from the air and water. Moreover, three elements of nitrogen, phosphorus, and potassium are absorbed from soil. However, since the existence thereof in soil is relatively small as compared with the amount to be absorbed by a plant, they tend to be depleted and effects easily appear when they are externally supplied, so that they are called as three elements of fertilizer. For plants, other than the three elements of fertilizer, there are further essential elements, which specifically include magnesium, sulfur, and calcium classified into major elements and manganese, boron, iron, zinc, copper, molybdenum, chlorine, and nickel classified into minor elements. Moreover, also in human being, deficiency diseases have been known for iron, zinc, copper, manganese, and vanadium. In particular, iron is depleted in an extremely wide distribution as it is said that one third of women suffer from potential iron-deficiency anemia.

Iron (Fe) is involved in the activation of an enzyme as a divalent iron ion ($Fe^{2+}$). Moreover, iron enters into a porphyrin ring to be transformed into heme and heme is present at active centers of various enzymes. Heme iron-containing proteins include cytochromes, peroxidases, and catalases, and iron-sulfur proteins include ferredoxins, which are involved in mainly oxidation-reduction reactions and electron transfer reactions. Chlorophyll is a substance wherein magnesium ion enters in a porphyrin ring. With regard to a protoporphyrinogen synthetic enzyme and a protochlorophyllide synthetic enzyme as precursor substances of the porphyrin ring synthesis, iron is considered to be involved in the control at a gene level. Therefore, when iron is deficient, the synthesis of porphyrin is inhibited and chlorophyll is not synthesized, so that a plant exhibits chlorosis, cannot perform photosynthesis, and finally is blighted.

Copper forms a constitutional component of tissues or a part of enzymes involved in metabolisms in a plant body. Common symptoms of its deficiency include chlorosis, necrosis, curly leaves, and the like. Plants exhibiting copper deficiency in farm fields include cultivated plants such as barley, wheat, alfalfa, lettuce, carrot, onion, tomato, tobacco, and citrus.

Manganese has physiological actions such as photosynthesis, respiration, and activation of oxygen and, in many plants, respiration increases as the amount of manganese increases in the plant bodies. When manganese is deficient, chlorosis is observed on leaves.

With regard to zinc, a large number of zinc enzymes and the like have been found and many in vivo reactions involving zinc are also known. As symptoms of its deficiency, suppression of elongation growth, inhibition of protein synthesis, and the like are observed at various sites of a variety of plants.

On the other hand, also in human being, importance of mineral intake has been perceived. According to Nihonjin no Shokuji Sesshu Kijun (Dietary Intake Standard of the Japanese) (Non-Patent Document 1), for example, a new index "desired amount" is set for calcium as a nutrient to be increased and also estimated average necessary amounts and recommended amounts are determined for other minerals. Moreover, osteoporosis has been hitherto pointed out owing to deficient intake of calcium but it has been found that only ingestion of calcium is not a sufficient countermeasure and magnesium and the like are also necessary.

However, at present, the intake of magnesium and calcium is about 100 mg lower than the recommended amount in Dietary Intake Standard of the Japanese. Moreover, in the other minerals, though copper is sufficient, the intake of iron and zinc is lower than the recommended amounts in sex and/or some ages.

As methods for ingesting minerals, there may be mentioned a method for ingestion with supplements and a method for ingestion with meals. In general, minerals have characteristics that the width of zone of appropriate intake is narrow and a balance between minerals is apt to be disrupted. The method for ingestion with supplements causes a problem that overdose disorder owing to excessive ingestion of a specific mineral occurs. Mineral overdose induced by the method for ingestion with meals is rare other than the case of sodium overdose with sodium chloride and it is easy to ingest minerals with good balance. Accordingly, as a method for ingesting minerals, it is preferred to ingest minerals with meals in just proportion.

Since vegetables abundantly contain various minerals and vitamins, vegetables are main sources of minerals in meals. However, according to Shokuryo Jukyu Hyo (Food Supply and Demand Table) (Non-Patent Document 2), it is reported that vegetable intake per day has decreased with the change in dietary habit and only an average of 250 g of vegetables is ingested although 350 g thereof per day is required. Thus, in order to increase mineral intake, it is desired to increase the mineral content in vegetables.

As a technology for enhancing metal component absorption in a plant, it has been reported that benzoic acid and/or benzoic acid derivatives enhance absorption of potassium ion (Patent Document 1). Moreover, there is a report that absorption of calcium ion is enhanced by spraying on the surface of leaves together with an aqueous amino acid solution (Patent Document 2) but any substance is not known, by which enhanced absorption of the other metal component(s) is observed.

Patent Document 1: JP-A-2002-284607
Patent Document 2: JP-A-2001-192310
Non-Patent Document 1: Nihonjin no Eiyo Shoyouryo-Shokuji Sesshu Kijun-Sakutei Kentoukai, Nihonjin no Shokuji Sesshu Kijun (Dietary Intake Standard of the Japanese) (2005)
Non-Patent Document 2: 2004, Ministry of Agriculture, Forestry and Fisheries, General Food Policy Bureau, March 2006: Shokuryo Jukyu Hyo (Food Supply and Demand Table)

DISCLOSURE OF THE INVENTION

Problems that the Invention is to Solve

Accordingly, an object of the invention is to provide an absorption enhancer of at least one metal component selected from the elements belonging to the groups 2 to 12 in the third to fourth periods necessary to a plant.

Means for Solving the Problems

Under such a situation, as a result of extensive studies, the present inventors have unexpectedly found that 5-aminolevulinic acid, a derivative thereof, or a salt thereof has no effect at a concentration of 30 ppm or more but exhibits an excellent metal component absorption enhancing action in the case of a treatment at a low concentration of 0.001 to 20 ppm, and thus they have accomplished the invention.

Namely, the invention provide an absorption enhancer of at least one metal component selected from the elements belonging to the groups 2 to 12 in the third to fourth periods in a plant, wherein the absorption enhancer comprises 5-aminolevulinic acid or a derivative thereof represented by the following general formula (1), or a salt thereof as an active ingredient:

   (1)

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group, an acyloxy group, an alkoxycarbonyloxy group, an aryloxy group, an aralkyloxy group, or an amino group, and the absorption enhancer is used for performing a treatment with the 5-aminolevulinic acid, the derivative thereof, or the salt thereof in a concentration of 0.001 to 20 ppm per each time.

Also, the invention provides a method for increasing the content of at least one metal component selected from the elements belonging to the groups 2 to in the third to fourth periods in a plant, which comprises treating roots or stems and leaves of a plant or surrounding soil or water with 5-aminolevulinic acid or a derivative thereof represented by the following general formula (1), or a salt thereof in a concentration of 0.001 to 20 ppm per each time:

   (1)

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group, an acyloxy group, an alkoxycarbonyloxy group, an aryloxy group, an aralkyloxy group, or an amino group.

Advantage of the Invention

The metal component absorption enhancer of the invention can prevent metal deficiency of a plant by enhancing absorption of at least one metal component selected from the elements belonging to the groups 2 to 12 in the third to fourth periods in a plant and also can increase metal(s), which is ingested by human being from a plant through a meal, by increasing at least one metal component selected from the elements belonging to the groups 2 to 12 in the third to fourth periods in a plant.

BEST MODE FOR CARRYING OUT THE INVENTION

Figure 1:
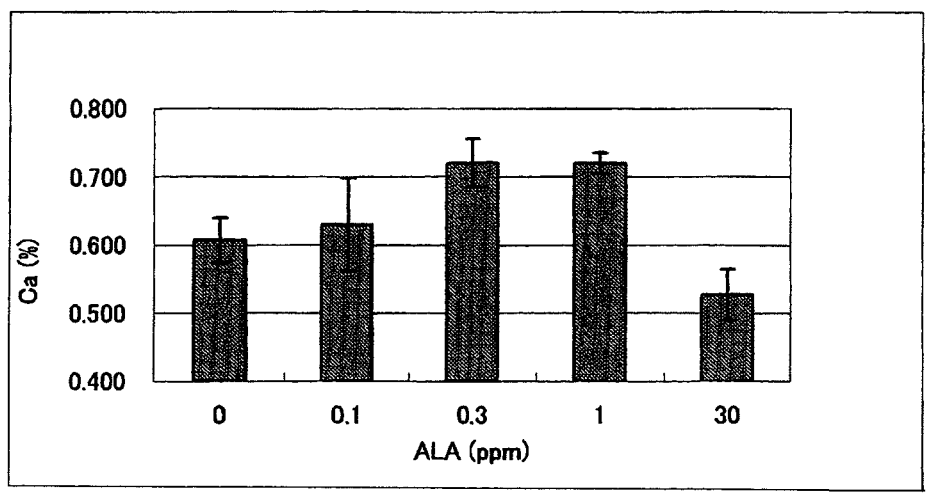
FIG. 1 is a figure showing a calcium content-enhancing effect in barley by the action of 5-aminolevulinic acid hydrochloride (shown as ALA in the figure, the same shall apply hereinafter).

The active ingredient of the metal component absorption enhancer of the invention is 5-aminolevulinic acid, a derivative thereof (the above general formula (1)), or a salt thereof.

The alkyl group represented by $R^1$ and $R^2$ in the general formula (1) is preferably a linear or branched alkyl group having 1 to 24 carbon atoms, more preferably an alkyl group having 1 to 18 carbon atoms, and particularly, an alkyl group having 1 to 6 carbon atoms is preferred. As the alkyl group having 1 to 6 carbon atoms, there may be mentioned a methyl group, an ethyl group, an n-propyl group, an isopropyl group, an n-butyl group, a sec-butyl group, and the like. As the acyl group, a linear or branched alkanoyl group having 1 to 12 carbon atoms, an alkenylcarbonyl group, or an aroyl group is preferred, and particularly, an alkanoyl group having 1 to 6 carbon atoms is preferred. As the acyl group, there may be mentioned a formyl group, an acetyl group, a propionyl group, a butyryl group, and the like. As the alkoxycarbonyl group, an alkoxycarbonyl group having 2 to 13 carbon atoms in total is preferred, and particularly, an alkoxycarbonyl group having 2 to 7 carbon atoms is preferred. As the alkoxycarbonyl group, there may be mentioned a methoxycarbonyl group, an ethoxycarbonyl group, an n-propoxycarbonyl group, an isopropoxycarbonyl group, and the like. As the aryl group, an aryl group having 6 to 16 carbon atoms is preferred and there may be, for example, mentioned a phenyl group, a naphthyl group, and the like. As the aralkyl group, a group composed of an aryl group having 6 to 16 carbon atoms and the above alkyl group having 1 to 6 carbon atoms is preferred and there may be, for example, mentioned a benzyl group and the like.

The alkoxy group represented by $R^3$ is preferably a linear or branched alkoxy group having 1 to 24 carbon atoms, more preferably an alkoxy group having 1 to 16 carbon atoms, and particularly, an alkoxy group having 1 to 12 carbon atoms is preferred. As the alkoxy group, there may be mentioned a methoxy group, an ethoxy group, an n-propoxy group, an isopropoxy group, an n-butoxy group, a pentyloxy group, a hexyloxy group, an octyloxy group, a decyloxy group, a dodecyloxy group, and the like. As the acyloxy group, a linear or branched alkanoyloxy group having 1 to 12 carbon atoms is preferred, and particularly, an alkanoyloxy group having 1 to 6 carbon atoms is preferred. As the acyloxy group, there may be mentioned an acetoxy group, a propionyloxy group, a butyryloxy group, and the like. As the alkoxycarbonyloxy group, an alkoxycarbonyloxy group having 2 to 13 carbon atoms in total is preferred, and particularly, an alkoxycarbonyloxy group having 2 to 7 carbon atoms in total is preferred. As the alkoxycarbonyloxy group, there may be mentioned a methoxycarbonyloxy group, an ethoxycarbonyloxy group, an n-propoxycarbonyloxy group, an isopropoxycarbonyloxy group, and the like. As the aryloxy group, an aryloxy group having 6 to 16 carbon atoms is preferred, and there may be, for example, mentioned a phenoxy group, a naphthyloxy group, and the like. As the aralkyloxy group, one having the above aralkyl group is preferred, and there may be, for example, mentioned a benzyloxy group and the like.

As $R^1$ and $R^2$ in the general formula (1), a hydrogen atom is preferred. As $R^3$, a hydroxyl group, an alkoxy group, or an aralkyloxy group is preferred, and more preferably, a hydroxyl group or an alkoxy group having 1 to 12 carbon atoms and particularly, a methoxy group or a hexyloxy group is preferred.

As the derivative of 5-aminolevulinic acid, there may be mentioned 5-aminolevulinic acid methyl ester, 5-aminolevulinic acid ethyl ester, 5-aminolevulinic acid propyl ester, 5-aminolevulinic acid butyl ester, 5-aminolevulinic acid pentyl ester, 5-aminolevulinic acid hexyl ester, and the like. Particularly, 5-aminolevulinic acid methyl ester or 5-aminolevulinic acid hexyl ester is preferred.

As the salt of 5-aminolevulinic acid or the derivative thereof, there may be, for example, mentioned acid addition salts such as hydrochlorides, phosphates, nitrates, sulfates, acetates, propionates, butyrates, valerates, citrates, fumarates, maleates, and malates; and metal salts such as sodium salts, potassium salts, and calcium salts. These salts are used as aqueous solutions at their use and their action is the same as in the case of 5-aminolevulinic acid. Any of 5-aminolevulinic acid and salts thereof may be used singly or two or more thereof may be used in combination.

5-Aminolevulinic acid, the derivative thereof, or the salt thereof is a known compound and can be produced by any method of chemical synthesis, production by a microorganism, and production by an enzyme. A product therefrom can be used as it is without separation and purification unless it contains harmful substance(s). In the case where it contains harmful substance(s), it can be used after the harmful substance(s) is suitably removed to a level where no harmful action is observed.

The plants to be targeted for application of the metal component absorption enhancer of the invention are not particularly limited and there may be mentioned plants widely cultivated in agricultural fields. Examples thereof include cereals such as rice, barley, wheat, Japanese barnyard millet, maize, and foxtail millet; vegetables such as pumpkin, turnip, cabbage, daikon radish, Chinese cabbage, spinach, komatsuna (*Brassica rapa* var. *peruviridis*), honewort, asparagus, broccoli, chive, celery, lettuce, garland chrysanthemum, potherb mustard, qing-geng-cai, bell pepper, tomato, eggplant, cucumber, and okra (*Abelmoschus esculentus*); fruits such as mandarin orange, apple, Japanese persimmon, Japanese apricot, pear, grape, peach, strawberry, water melon, and melon; flowers such as chrysanthemum, gerbera, pansy, orchid, peony root, and tulip; trees such as *Rhododendron indicum*, sawtooth oak, Japanese cedar (*Cryptomeria japonica*), Japanese cypress, oak, and beech; beans such as adzuki bean, common bean, soy bean, peanut, broad bean, and garden pea; turf grasses such as *Zoysia matrella*, bent grass, and Japanese lawn grass; potatoes such as potato, sweet potato, aroid, yam, and taro; scallions such as scallion, Wakegi green onion, onion, and Rakkyo (*Allium chinense*); pasture grasses such as alfalfa, clover, and Chinese milk vetch; and root vegetables such as carrot, daikon radish, radish, turnip, and edible burdock. Cereals, vegetables, root vegetables, and potatoes are preferred, and spinach, barley, radish, and potato are more preferred.

In the invention, as the elements belonging to the groups 2 to 12 in the third to fourth periods, there may be mentioned magnesium, calcium, vanadium, manganese, iron, copper and zinc, and germanium, and preferred are magnesium, calcium, manganese, iron, copper, and zinc. Particularly, the absorption enhancer of the invention is suitably used for enhancing iron absorption.

In the invention, as the metal component absorption enhancer, 5-aminolevulinic acid, a derivative thereof, or a salt thereof alone may be used but, in addition thereto, a plant growth regulator, a sugar, an amino acid, an organic acid, an alcohol, a vitamin, a mineral, and/or the like can be mixed. As the plant growth regulator to be used herein, there may be, for example, mentioned brassinolides such as epibrassinolide, choline agents such as choline chloride and choline nitrate, indolebutyric acid, indoleacetic acid, ethychlozate agent, 1-naphthylacetamide agent, isoprothiolane agent, nicotinic acid amide agent, hydroxyisoxazole agent, calcium peroxide agent, benzylaminopurine agent, methasulfocarb agent, oxyethylene docosanol agent, ethephon agent, chlochinphonac agent, gibberellin, streptomycin agent, daminozide agent, benzylaminopurine agent, 4-chlorophenoxyacetic acid (4-CPA) agent, ancymidol agent, inabenfide agent, uniconazole agent, chlormequat agent, dikeblack agent, mefluidide agent, calcium carbonate agent, piperonyl butoxide agent, and the like.

As the sugar, there may be, for example, mentioned glucose, sucrose, xylitol, sorbitol, galactose, xylose, mannose, arabinose, madurose, sucrose, ribose, rhamnose, fructose, maltose, lactose, maltotriose, and the like.

As the amino acid, there may be, for example, mentioned asparagine, glutamine, histidine, tyrosine, glycine, arginine, alanine, tryptophan, methionine, valine, proline, leucine, lysine, isoleucine, and the like.

As the organic acid, there may be, for example, mentioned formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, $\alpha$-ketoglutaric acid, levulinic acid, and the like.

As the alcohol, there may be, for example, mentioned methanol, ethanol, propanol, butanol, pentanol, hexanol, glycerol, and the like.

As the vitamin, there may be, for example, mentioned nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, $\alpha$-tocopherol, $\beta$-tocopherol, $\gamma$-tocopherol, $\sigma$-tocopherol, p-hydroxybenzoic acid, biotin, folic acid, nicotinic acid, pantothenic acid, $\alpha$-lipoic acid, and the like.

As the mineral, there may be, for example, mentioned nitrogen, phosphorus, potassium, calcium, boron, manganese, magnesium, zinc, copper, iron, molybdenum, magnesium, and the like.

The metal component absorption enhancer of the invention contains 5-aminolevulinic acid, a derivative thereof, or a salt thereof and the treatment concentration per each time is 0.001 to 20 ppm as the 5-aminolevulinic acid, the derivative thereof, or the salt thereof. In the case where the treatment concentration is less than 0.001 ppm and in the case where the concentration is more than 20 ppm, the metal component absorption effect is not sufficient in both cases. Particularly preferred treatment concentration is 0.01 to 10 ppm.

The metal component absorption enhancer of the invention is used through the treatment of roots or stems and leaves of a plant or surrounding soil or water. Specifically, the enhancer may be used for foliage treatment (a foliage-treating agent) or may be used for soil treatment (a soil-treating agent). Moreover, the enhancer may be absorbed before a plant is planted or a cutting is planted. Furthermore, the enhancer may be added into water at hydroponics.

In the case where the enhancer is used as a foliage-treating agent, it is preferred that 5-aminolevulinic acid, a derivative thereof, or a salt thereof is incorporated in a concentration of preferably 0.001 to 20 ppm, more preferably 0.01 to 10 ppm, particularly preferably 0.1 to 5 ppm, further preferably 0.2 to 1.5 ppm and is used in a ratio of 10 to 1000 L, particularly 50 to 300 L per 10 are. The kind and amount of the spreading agent to be used for a plant such as monocotyledon to which the foliage-treating agent is hardly attached to its leave surfaces are not particularly limited.

In the case where the enhancer is used as a soil-treating agent, it is preferred to use 5-aminolevulinic acid, a derivative thereof, or a salt thereof in a ratio of preferably 0.1 to 20000 mg, more particularly 10 to 10000 mg, particularly preferably 100 to 5000 mg, further preferably 200 to 1500 mg per 10 are. As concentration, preferred is 0.001 to 20 ppm, more preferred is 0.01 to 10 ppm, particularly preferred is 0.1 to 5 ppm, and further preferred is 0.2 to 1.5 ppm. It is preferred to use the agent having a concentration of the above range in an amount of 10 to 1000 L per 10 are.

In the case where 5-aminolevulinic acid, a derivative thereof, or a salt thereof is added to a water culture medium, it is desired that the concentration of the 5-aminolevulinic acid, the derivative thereof, or the salt thereof is preferably 0.001 to 20 ppm, more preferably 0.01 to 10 ppm, particularly preferably 0.05 to 5 ppm, further preferably 0.1 to 3 ppm

EXAMPLES

The following will specifically describe the invention with reference to Examples but they are cited only for illustration and do not limited the invention.

Example 1

Calcium Absorption-Enhancing Effect of 5-Aminolevulinic Acid

Two containers were provided and soil was placed in each of them, in which seeds of spinach were uniformly planted. From the day when the seeds were planted, water was applied once a day by means of a sprinkling can. To one of the container, tap water in which 5-aminolevulinic acid hydrochloride was dissolved in a concentration of 1 ppm was sprayed once a day in an amount of about 50 mL by means of a sprayer. Thinning was performed 3 weeks after the seed planting, and harvest was performed on the two containers after 38 days. At the harvest, the upper portions from the ground were cut out and the plant bodies were subjected to natural drying. After drying, the plant bodies was ground one by one in a mortar, the calcium content in dry weight was measured by ICP, and the concentration was calculated. Table 1 shows average values of calcium concentration for the case where 5-aminolevulinic acid was added and for the case where it was not added.

TABLE 1

| Average value of calcium concentration in spinach (%) ||
|---|---|
| Administration of 5-aminolevulinic acid (n = 18) | No 5-aminolevulinic acid (n = 22) |
| 0.68 | 0.61 |

As shown in Table 1, a calcium content-enhancing effect was observed in spinach by the spraying of 5-aminolevulinic acid hydrochloride and thus it was fond that the compound is useful as a metal component absorbent.

Example 2

Manganese Absorption-Enhancing Effect of 5-Aminolevulinic Acid

Similar operations were performed as in Example 1 and the manganese concentration in spinach was calculated. The results are shown in Table 2.

TABLE 2

| Average value of manganese concentration in spinach (%) ||
|---|---|
| Administration of 5-aminolevulinic acid (n = 18) | No 5-aminolevulinic acid (n = 22) |
| 0.031 | 0.027 |

As shown in Table 2, a manganese content-enhancing effect was observed in spinach by the spraying of 5-aminolevulinic acid hydrochloride and thus it was fond that the compound is useful as a metal component absorbent.

Example 3

Iron Absorption-Enhancing Effect of 5-Aminolevulinic Acid

Similar operations were performed as in Example 1 and the iron concentration in spinach was calculated. The results are shown in Table 3.

TABLE 3

| Average value of iron concentration in spinach (%) ||
|---|---|
| Administration of 5-aminolevulinic acid (n = 18) | No 5-aminolevulinic acid (n = 22) |
| 0.049 | 0.015 |

As shown in Table 3, an iron content-enhancing effect was observed in spinach by the spraying of 5-aminolevulinic acid hydrochloride and thus it was fond that the compound is useful as a metal component absorbent.

Example 4

Copper Absorption-Enhancing Effect of 5-Aminolevulinic Acid

Similar operations were performed as in Example 1 and the copper concentration in spinach was calculated. The results are shown in Table 4.

TABLE 4

| Average value of copper concentration in spinach (%) ||
| --- | --- |
| Administration of 5-aminolevulinic acid (n = 18) | No 5-aminolevulinic acid (n = 22) |
| 0.029 | 0.023 |

As shown in Table 4, a copper content-enhancing effect was observed in spinach by the spraying of 5-aminolevulinic acid hydrochloride and thus it was fond that the compound is useful as a metal component absorbent.

Example 5

Zinc Absorption-Enhancing Effect of 5-Aminolevulinic Acid

Similar operations were performed as in Example 1 and the zinc concentration in spinach was calculated. The results are shown in Table 5.

TABLE 5

| Average value of zinc concentration in spinach (%) ||
| --- | --- |
| Administration of 5-aminolevulinic acid (n = 18) | No 5-aminolevulinic acid (n = 22) |
| 0.048 | 0.033 |

As shown in Table 5, a zinc content-enhancing effect was observed in spinach by the spraying of 5-aminolevulinic acid hydrochloride and thus it was fond that the compound is useful as a metal component absorbent.

Example 6

Calcium Absorption-Enhancing Effect of 5-Aminolevulinic Acid

Barley (race: Fiber snow) was seeded on river sand, sprouted, and grown for 9 days. After the growth, the sand was washed out with caring so as not to hurt roots and the roots were cut so as to adjust the length to 2 cm. The roots were immersed in a water culture medium A and hydroponics was performed. Table 6 shows the composition of the water culture medium A.

As water culture media, one in which no 5-aminolevulinic acid was dissolved and those in which the compound was dissolved so that each one has a concentration of 0.1, 0.3, or 1 ppm were prepared. The water culture medium was replaced 13 days after the start of the hydroponics, and hydroponics was continued for another 6 days. After the hydroponics, the plant was dried at 50° C. for two nights and then was subjected to ICP metal analysis. The results are shown in FIG. 1.

TABLE 6

| Used salt | g/L |
| --- | --- |
| $NH_4NO_3$ | 0.028575 |
| $NaNO_3$ | 0.0425 |
| $NaH_2PO_4 \cdot 2H_2O$ | 0.0126 |
| $K_2SO_4$ | 0.04345 |
| $CaCl_2 \cdot 2H_2O$ | 0.073375 |
| $MgSO_4 \cdot 7H_2O$ | 0.12165 |
| DTPA-Fe | 0.002488 |

TABLE 6-continued

| Used salt | g/L |
| --- | --- |
| $MnSO_4 \cdot 5H_2O$ | 0.0011 |
| $H_2BO_3$ | 0.000713 |
| $ZnSO_4 \cdot 7H_2O$ | 0.000225 |
| $CuSO_4 \cdot 5H_2O$ | $8.75E^{-06}$ |
| $(NH_4)_6Mo_7O_{24} \cdot 4H_2O$ | $2.25E^{-06}$ |

As shown in FIG. 1, a calcium content-enhancing effect was observed in barley by the addition of 5-aminolevulinic acid hydrochloride to the water culture medium and thus it was fond that the compound is useful as a metal component absorbent.

Example 7

Manganese Absorption-Enhancing Effect of 5-Aminolevulinic Acid

Similar operations were performed as in Example 6 except that the concentration of the added 5-aminolevulinic acid was adjusted to 0, 0.3, or 1 ppm and the manganese concentration in barley was analyzed. The results are shown in FIG. 2.

Figure 2:
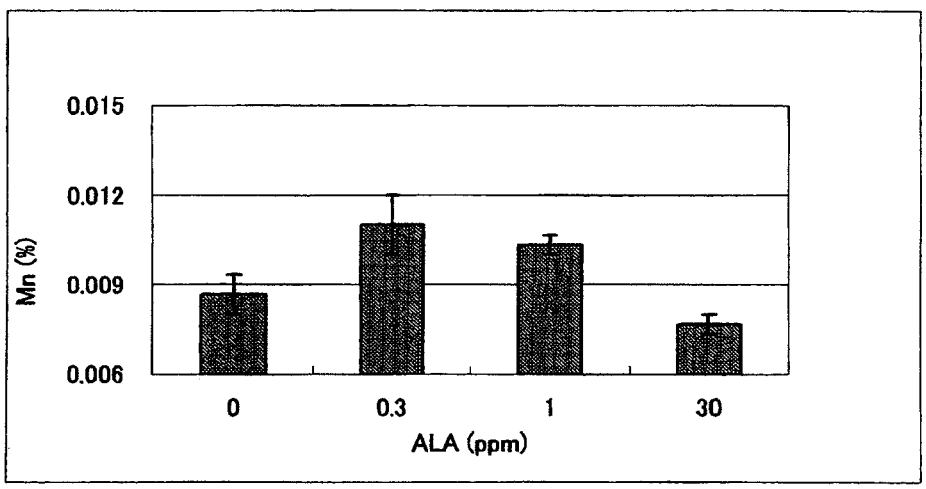
FIG. 2 is a figure showing a manganese content-enhancing effect in barley by the action of 5-aminolevulinic acid hydrochloride.

As shown in FIG. 2, a manganese content-enhancing effect was observed in barley by the addition of 5-aminolevulinic acid hydrochloride to the water culture medium and thus it was fond that the compound is useful as a metal component absorbent.

Example 8

Iron Absorption-Enhancing Effect of 5-Aminolevulinic Acid

Similar operations were performed as in Example 6 except that the composition of the water culture medium was changed to twofold concentration of the water culture medium A and the concentration of the added 5-aminolevulinic acid was adjusted to 0, 1, or 3 ppm, and then the iron concentration in barley was analyzed. The results are shown in FIG. 3.

Figure 3:
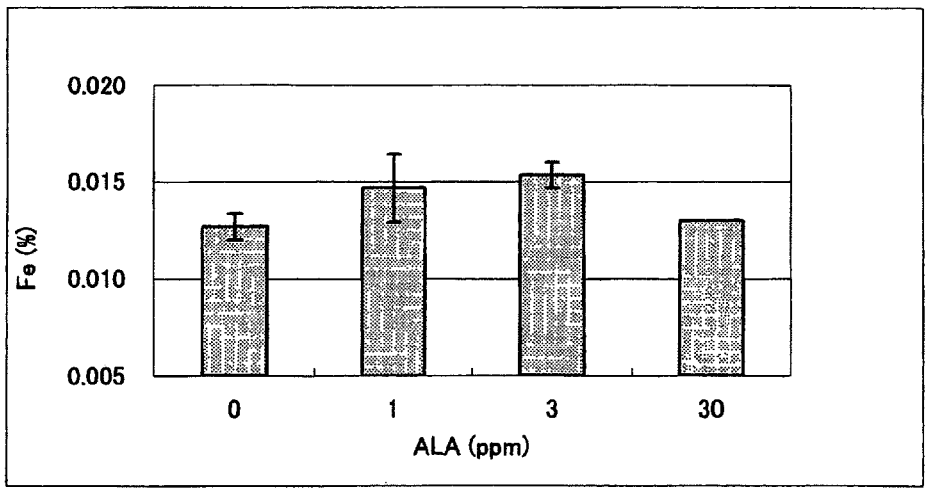
FIG. 3 is a figure showing an iron content-enhancing effect in barley by the action of 5-aminolevulinic acid hydrochloride.

As shown in FIG. 3, an iron content-enhancing effect was observed in barley by the addition of 5-aminolevulinic acid hydrochloride to the water culture medium and thus it was fond that the compound is useful as a metal component absorbent.

Example 9

Copper Absorption-Enhancing Effect of 5-Aminolevulinic Acid

Similar operations were performed as in Example 6 except that the water culture medium A and a water culture medium having a composition which was twice the composition of the water culture medium A were used and the concentration of the added 5-aminolevulinic acid was adjusted to 0, 0.1, or 0.3 ppm, and then the copper concentration in barley was analyzed. The results are shown in FIG. 4 (left one in the figure is for the water culture medium A and right one is for twofold concentration of the water culture medium A).

Figure 4:
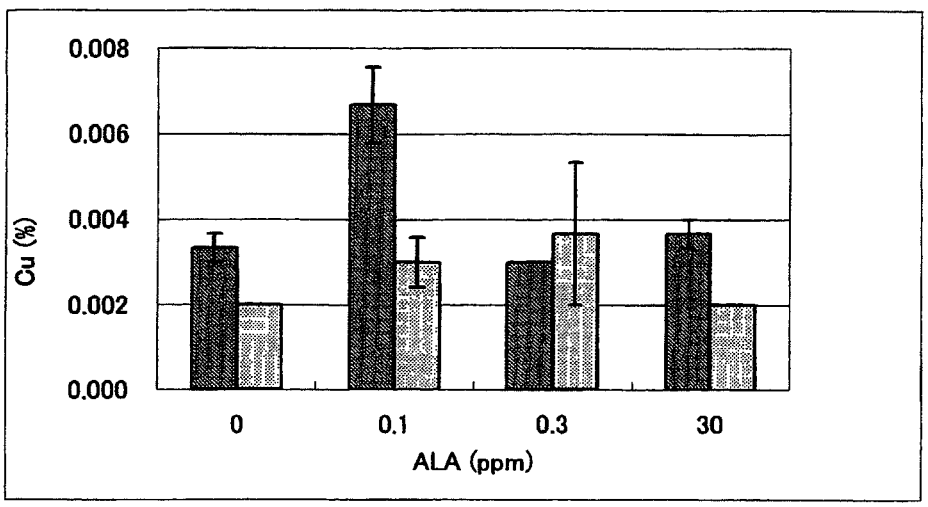
FIG. 4 is a figure showing a copper content-enhancing effect in barley by the action of 5-aminolevulinic acid hydrochloride.

As shown in FIG. 4, a copper content-enhancing effect was observed in barley by the addition of 5-aminolevulinic acid hydrochloride to the water culture medium and thus it was fond that the compound is useful as a metal component absorbent.

Example 10

Zinc Absorption-Enhancing Effect of 5-Aminolevulinic Acid

Similar operations were performed as in Example 6 except that the concentration of the added 5-aminolevulinic acid was adjusted to 0, 0.1, or 0.3 ppm, and the zinc concentration in barley was analyzed. The results are shown in FIG. 5.

Figure 5:
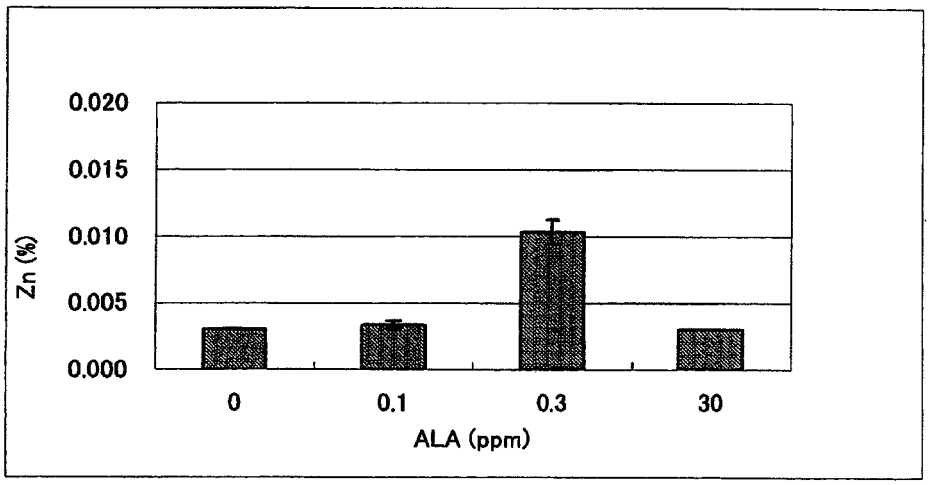
FIG. 5 is a figure showing zinc content-enhancing effect in barley by the action of 5-aminolevulinic acid hydrochloride.

As shown in FIG. 5, a zinc content-enhancing effect was observed in barley by the addition of 5-aminolevulinic acid hydrochloride to the water culture medium and thus it was fond that the compound is useful as a metal component absorbent.

Example 11

Magnesium Absorption-Enhancing Effect of 5-Aminolevulinic Acid

Similar operations were performed as in Example 6 except that the concentration of the added 5-aminolevulinic acid was adjusted to 0, 0.1, 0.3, 1, or 3 ppm, and the manganese concentration in barley was analyzed. The results are shown in FIG. 6.

Figure 6:
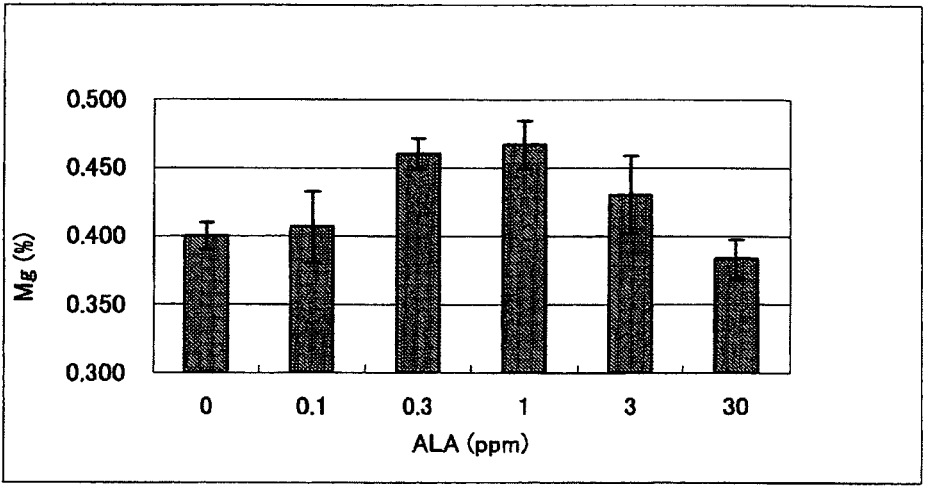
FIG. 6 is a figure showing a magnesium content-enhancing effect in barley by the action of 5-aminolevulinic acid hydrochloride.

As shown in FIG. 6, a magnesium content-enhancing effect was observed in barley by the addition of 5-aminolevulinic acid hydrochloride to the water culture medium and thus it was fond that the compound is useful as a metal component absorbent.

Example 12

Manganese Absorption-Enhancing Effect of 5-Aminolevulinic Acid

Radish was sowed in a pot of 1/57000×10 are in an amount of 6 seeds per pot and grown. An andosol (Kuroboku-soil) was used as soil and watering was suitably performed. On 11th day after the seeding (a two true leaves-developed stage), a solution containing 5-aminolevulinic acid hydrochloride prepared to a concentration of 0, 1, or 10 ppm in a developing agent-diluted (2000 times) liquid was applied to foliage treatment. Moreover, on this occasion, DTPA iron and magnesium sulfate were transformed into solutions having a concentration of 1.8 and 4.5 ppm in terms of Fe and MgO, respectively, and were applied to foliage treatment together with 5-aminolevulinic acid hydrochloride. The amount used for the treatment was 100 L per 10 are. The number of pots was 5 pots per test plot. On 15th day and 20th day after the seeding, thinning was performed and the number of plants per pot was adjusted to 4 individuals. On 25th day after the seeding, the plants were harvested and completely dried at 50° C. for two nights. Thereafter, they are pulverized and mixed in a mixer and then IPC metal analysis was performed. The results are shown in FIG. 7.

Figure 7:
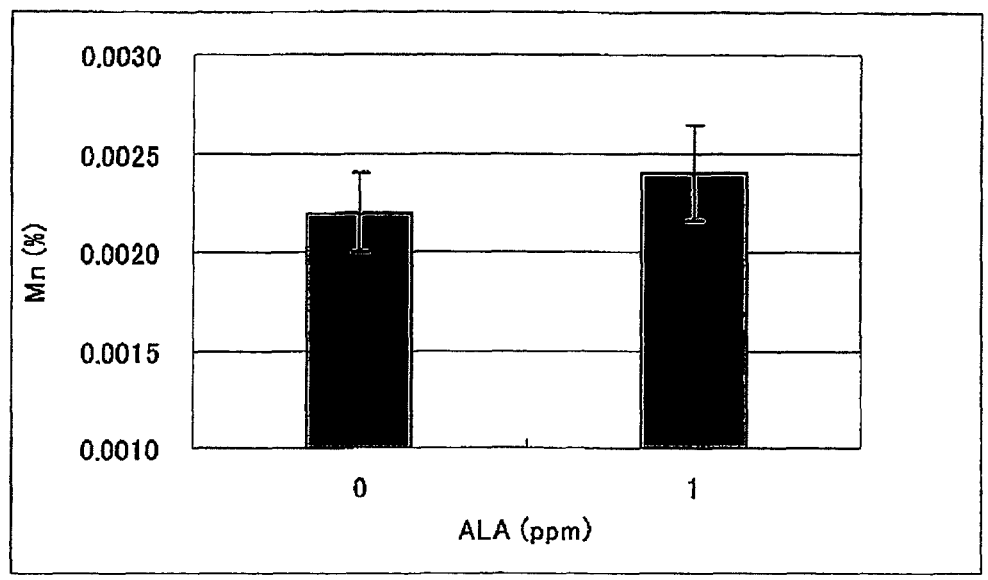
FIG. 7 is a figure showing a manganese content-enhancing effect in radish by the action of 5-aminolevulinic acid hydrochloride.

As shown in FIG. 7, a manganese content-enhancing effect was observed in radish by the application of 5-aminolevulinic acid hydrochloride to the foliage treatment and thus it was fond that the compound is useful as a metal component absorbent.

Example 13

Zinc Absorption-Enhancing Effect of 5-Aminolevulinic Acid

Similar operations were performed as in Example 12 and the zinc concentration in radish was analyzed. The results are shown in FIG. 8.

Figure 8:
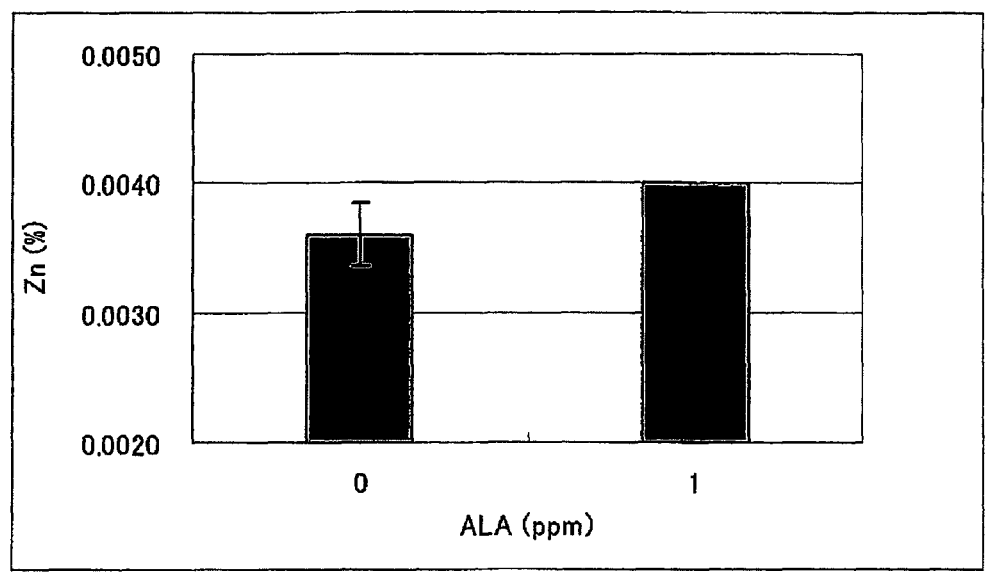
FIG. 8 is a figure showing a zinc content-enhancing effect in radish by the action of 5-aminolevulinic acid hydrochloride.

As shown in FIG. 8, a zinc content-enhancing effect was observed in radish by the application of 5-aminolevulinic acid hydrochloride to the foliage treatment and thus it was fond that the compound is useful as a metal component absorbent.

Example 14

Iron Absorption-Enhancing Effect of 5-Aminolevulinic Acid

A seed tuber of potato was subjected to light-exposure and sprout-growth to stimulate germination. The germinated potato was planted in a pot of 1/20000×10 are in an amount of 1 tuber per pot. On 30th day after the planting (height of terrestrial portion: about 30 cm), 5-Aminolevulinic Acid hydrochloride was dissolved in a developing agent-diluted (2000 times) liquid in a concentration of 0 or 1 ppm and was applied to foliage treatment. Thereafter, the foliage treatment was performed 8 times every other week. The number of pots was 3 pots per test plot and new sprouts were removed while a strong thick sprout was left so that the number of sprout per pot was 1. On 105th day after the planting, potato as tubers was harvested and the tubers were selected from each test plot so that the total weight was 120±10 g. Then, they were pared and completely dried at 50° C. for two nights. Thereafter, they are pulverized and mixed in a mixer and then IPC metal analysis was performed. The results are shown in FIG. 9.

Figure 9:
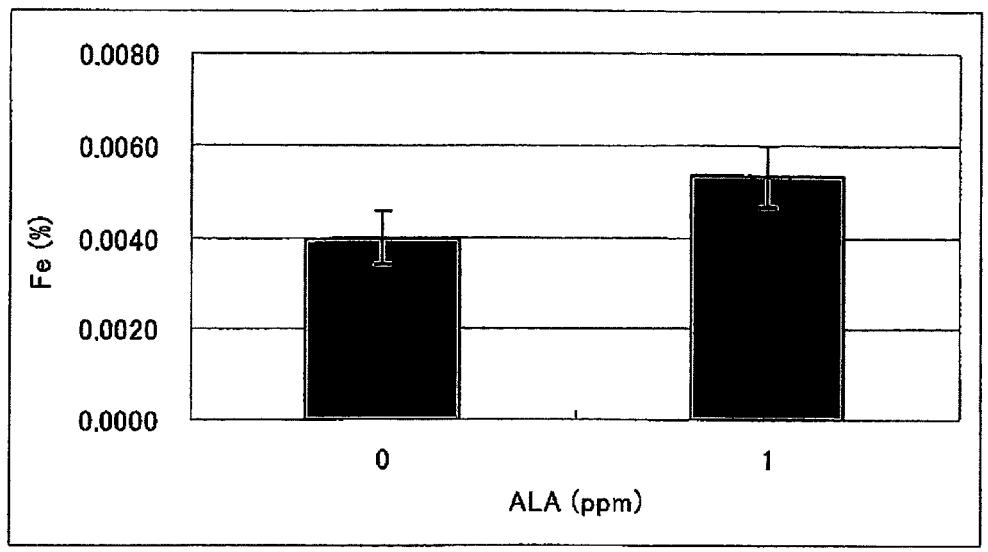
FIG. 9 is a figure showing an iron content-enhancing effect in potato by the action of 5-aminolevulinic acid hydrochloride.

As shown in FIG. 9, an iron content-enhancing effect was observed in potato by the application of 5-aminolevulinic acid hydrochloride to the foliage treatment and thus it was fond that the compound is useful as a metal component absorbent.

Example 15

Magnesium Absorption-Enhancing Effect of 5-Aminolevulinic Acid

Similar operations were performed as in Example 14 and the magnesium concentration in potato was analyzed. The results are shown in FIG. 10.

Figure 10:
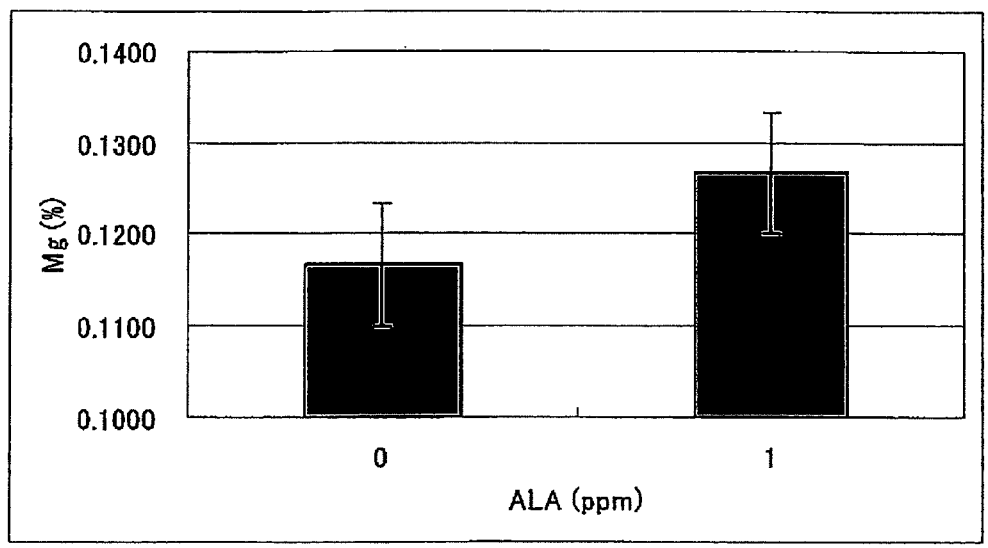
FIG. 10 is a figure showing magnesium content-enhancing effect in potato by the action of 5-aminolevulinic acid hydrochloride.

As shown in FIG. 10, a magnesium content-enhancing effect was observed in potato by the application of 5-aminolevulinic acid hydrochloride to the foliage treatment and thus it was fond that the compound is useful as a metal component absorbent.

Comparative Example 1

Calcium Absorption-Enhancing Effect of 5-Aminolevulinic Acid

Similar operations were performed as in Example 6 except that the concentration of the added 5-aminolevulinic acid was adjusted to 0 or 30 ppm, and the calcium concentration in barley was analyzed. The results are shown in FIG. 1.

As shown in FIG. 1, a calcium content-enhancing effect was not observed in barley in the case where 5-aminolevulinic acid hydrochloride was added to the water culture medium in a concentration of 30 ppm.

Comparative Example 2

Manganese Absorption-Enhancing Effect of 5-Aminolevulinic Acid

Similar operations were performed as in Example 6 except that the concentration of the added 5-aminolevulinic acid was adjusted to 0 or 30 ppm, and the manganese concentration in barley was analyzed. The results are shown in FIG. 2.

As shown in FIG. 2, a manganese content-enhancing effect was not observed in barley in the case where 5-aminolevulinic acid hydrochloride was added to the water culture medium in a concentration of 30 ppm.

Comparative Example 3

Iron Absorption-Enhancing Effect of 5-Aminolevulinic Acid

Similar operations were performed as in Example 6 except that the concentration of the added 5-aminolevulinic acid was adjusted to 0 or 30 ppm and the iron concentration in barley was analyzed. The results are shown in FIG. 3.

As shown in FIG. 3, an iron content-enhancing effect was not observed in barley in the case where 5-aminolevulinic acid hydrochloride was added to the water culture medium in a concentration of 30 ppm.

Comparative Example 4

Copper Absorption-Enhancing Effect of 5-Aminolevulinic Acid

Similar operations were performed as in Example 6 except that the concentration of the added 5-aminolevulinic acid was adjusted to 0 or 30 ppm, and the copper concentration in barley was analyzed. The results are shown in FIG. 4.

As shown in FIG. 4, a copper content-enhancing effect was not observed in barley in the case where 5-aminolevulinic acid hydrochloride was added to the water culture medium in a concentration of 30 ppm.

Comparative Example 5

Zinc Absorption-Enhancing Effect of 5-Aminolevulinic Acid

Similar operations were performed as in Example 6 except that the concentration of the added 5-aminolevulinic acid was adjusted to 0 or 30 ppm, and the zinc concentration in barley was analyzed. The results are shown in FIG. 5.

As shown in FIG. 5, a zinc content-enhancing effect was not observed in barley in the case where 5-aminolevulinic acid hydrochloride was added to the water culture medium in a concentration of 30 ppm.

Comparative Example 6

Magnesium Absorption-Enhancing Effect of 5-Aminolevulinic Acid

Similar operations were performed as in Example 6 except that the concentration of the added 5-aminolevulinic acid was adjusted to 0 or 30 ppm and the magnesium concentration in barley was analyzed. The results are shown in FIG. 6.

As shown in FIG. 6, a magnesium content-enhancing effect was not observed in barley in the case where 5-aminolevulinic acid hydrochloride was added to the water culture medium in a concentration of 30 ppm.

While the invention has been described in detail and with reference to specific embodiments thereof, it will be apparent to one skilled in the art that various changes and modifications can be made therein without departing from the spirit and scope thereof.

The present application is based on Japanese Patent Application No. 2007-189879 filed on Jul. 20, 2007, and the contents are incorporated herein by reference.

INDUSTRIAL APPLICABILITY

According to the present invention, there can be provided an absorption enhancer of at least one metal component selected from the elements belonging to the groups 2 to 12 in the third to fourth periods necessary to a plant.

The invention claimed is:

1. A method for increasing the content of at least one metal component selected from the group consisting of the elements of manganese, iron, copper and zinc in a plant, which comprises treating the foliage of a plant with a composition containing 5-aminolevulinic acid or a derivative thereof represented by the following general formula (1), or a salt thereof in a concentration of 0.2 to 5 ppm per each time:

$$R^2R^1NCH_2COCH_2CH_2COR^3 \qquad (1)$$

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group, an acyloxy group, an alkoxycarbonyloxy group, an aryloxy group, an aralkyloxy group, or an amino group, wherein a soil or water culture medium in which the plant grows contains at least one metal component selected from the group consisting of the elements of manganese, iron, copper and zinc, and/or the composition further contains at least one metal component selected from the group consisting of the elements of manganese, iron, copper and zinc, whereby the content of at least one metal component selected from the group consisting of the elements of manganese, iron, copper and zinc in the plant is increased.

2. The method for increasing the content of a metal component according to claim 1, wherein the plant is selected from the group consisting of spinach, barley, radish and potato.

* * * * *